(12) United States Patent
Matsumoto et al.

(10) Patent No.: US 9,169,184 B2
(45) Date of Patent: Oct. 27, 2015

(54) METHOD FOR PRODUCING DITRIMETHYLOLPROPANE

(75) Inventors: Masami Matsumoto, Okayama (JP);
Hiroaki Shigeta, Okayama (JP);
Nozomi Nakagawa, Okayama (JP);
Ikutaro Kuzuhara, Kanagawa (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 282 days.

(21) Appl. No.: 13/820,586

(22) PCT Filed: Sep. 5, 2011

(86) PCT No.: PCT/JP2011/070177
§ 371 (c)(1),
(2), (4) Date: Apr. 3, 2013

(87) PCT Pub. No.: WO2012/033055
PCT Pub. Date: Mar. 15, 2012

(65) Prior Publication Data
US 2013/0184497 A1    Jul. 18, 2013

(30) Foreign Application Priority Data
Sep. 7, 2010 (JP) ................................ 2010-200087

(51) Int. Cl.
C07C 41/42 (2006.01)
C07C 41/01 (2006.01)
C07C 29/38 (2006.01)
C07C 41/40 (2006.01)

(52) U.S. Cl.
CPC ................. *C07C 41/42* (2013.01); *C07C 29/38* (2013.01); *C07C 41/01* (2013.01); *C07C 41/40* (2013.01)

(58) Field of Classification Search
None
See application file for complete search history.

(56) References Cited

U.S. PATENT DOCUMENTS

| 3,097,245 | A | | 7/1963 | Russell et al. |
| 3,740,322 | A | * | 6/1973 | Wada et al. ..................... 203/48 |
| 3,829,507 | A | * | 8/1974 | Zey ............................... 568/680 |
| 2002/0033325 | A1 | | 3/2002 | Ninomiya et al. |
| 2004/0254405 | A1 | | 12/2004 | Kuzuhara et al. |

FOREIGN PATENT DOCUMENTS

| JP | 47-30611 | 11/1972 |
| JP | 49-133311 | 12/1974 |
| JP | 8-157401 | 6/1998 |
| JP | 11-49708 | 2/1999 |
| JP | 2002-47231 | 2/2002 |
| JP | 2002-47232 | 2/2002 |
| JP | 2002-47233 | 2/2002 |
| JP | 2005-23067 | 1/2005 |
| WO | 2009/057466 | 5/2009 |

OTHER PUBLICATIONS

Search report from International Application No. PCT/JP2011/070177, mail date is Dec. 6, 2011.

* cited by examiner

*Primary Examiner* — Rosalynd Keys
(74) *Attorney, Agent, or Firm* — Greenblum & Bernstein, P.L.C.

(57) ABSTRACT

The present invention provides a method for producing ditrimethylolpropane which is characterized by the following (1) and (2): (1) a distillation still residue separated from purified trimethylolpropane is subjected to re-distillation under specific conditions to obtain a ditrimethylolpropane-containing solution having given contents of bis-TMP and tri-TMP; and (2) when subjecting the ditrimethylolpropane-containing solution to crystallization with an organic solvent, the crystallization is initiated under pressure at a temperature exceeding a boiling point of the organic solvent as measured under normal pressures, and the resulting crystallization product solution is cooled at a temperature drop rate of 2° C./min or less. According to the above method, it is possible to produce a high-purity ditrimethylolpropane from a distillation still residue obtained upon production of trimethylolpropane in a simple, industrially useful manner.

11 Claims, No Drawings

METHOD FOR PRODUCING DITRIMETHYLOLPROPANE

TECHNICAL FIELD

The present invention relates to a method for efficiently recovering ditrimethylolpropane from a reaction solution obtained by reacting n-butyl aldehyde and formaldehyde in the presence of a base catalyst.

BACKGROUND ART

For example, as described in Patent Document 1, when industrially producing trimethylolpropane (hereinafter also referred to as "TMP") by aldol condensation and crossed Cannizzaro reaction of n-butyl aldehyde (hereinafter also referred to as "NBD") and formaldehyde in the presence of a base catalyst, ditrimethylolpropane (hereinafter also referred to as "di-TMP"), tritrimethylolpropane (hereinafter also referred to as "tri-TMP") and bistrimethylolpropane (hereinafter also referred to as "bis-TMP") are by-produced, and the di-TMP is recovered from a high-boiling mixture thereof.

That is, as described in Patent Document 2, a TMP extract (crude TMP) containing substantially no sodium formate is obtained by extracting a reaction product solution obtained by the reaction of NBD and formaldehyde with a solvent after condensing or without condensing the reaction product solution.

Also, in Patent Document 3, there has been proposed the method in which 2-ethyl-2-propenal (hereinafter also referred to as "ECR") produced in the above reaction is recovered and reacted with TMP, ECR and formaldehyde to increase an amount of di-TMP produced.

To recover di-TMP from the crude di-TMP as a distillation still residue obtained upon production of TMP, there have been proposed crystallization using ethyl acetate (Patent Document 4), crystallization using water as a solvent in the presence of sodium formate (Patent Document 5), crystallization using 1,4-dioxane as a solvent (Patent Document 6), crystallization using water as a solvent after thin-film distillation (Patent Document 7), crystallization of di-TMP under specific conditions by adding an organic solvent to crude di-TMP (Patent Document 8), use of a water-insoluble or slightly water-soluble organic solvent having a di-TMP partition coefficient of 1 or more as a reaction solvent (Patent Document 9), and the like.

These methods for recovering di-TMP from crude di-TMP have the following problems.

(1) When using water as a solvent in the recrystallization from the crude di-TMP as described in Patent Documents 5 and 7, it is not possible to prevent the resulting crystals from being stained with coloring components. In addition, a mother liquor separated from the crystals is a waste water containing organic substances at a high concentration. Therefore, huge expenditure will be need for purification treatment of such a waste water. Also, huge expenditure of energy will be needed when subjecting the mother liquor to distillation to separate and reuse water contained therein. A combustion treatment of the waster water is also undesirable since such a treatment requires a very large amount of a secondary fuel.

(2) In the crystallization using an organic solvent such as ethyl acetate as described in Patent Document 4, it is not possible to obtain a high-purity di-TMP. In order to increase a purity of the obtained di-TMP, the crystallization procedure must be repeated, resulting in poor yield of di-TMP. In the crystallization using 1,4-dioxane as described in Patent Document 6, it is possible to obtain a high-purity di-TMP only by a single operation of the crystallization. However, the 1,4-dioxane is harmful and forms an explosive peroxide by reacting with oxygen in air. When recovering 1,4-dioxane by distillation to reuse the mother liquor separated after the crystallization, there is a risk of explosion thereof. Therefore, in the industrial procedure, it is desirable to avoid the use of 1,4-dioxane.

(3) When conducting the crystallization under the conditions as described in Patent Document 8, it is possible to efficiently separate and remove bis-TMP as an impurity from the crude di-TMP. However, in the crystallization procedure, it is required to render the reaction solution uniform before initiating the crystallization. For this reason, when the concentration of di-TMP in the crude di-TMP as a raw material is high, the use of a large amount of an organic solvent is required to prepare the uniform solution, so that an amount of a mother liquor produced after filtration of the reaction solution is increased, which tends to result in problems such as increased amount of a waste water, need of a very large amount of energy for recovery of the solvent, and low recovery rate owing to increase in amount of di-TMP distributed in the mother liquor.

(4) When it is intended to efficiently synthesize di-TMP in such a manner as described in Patent Document 9, a large amount of tri-TMP tends to be by-produced. In general, a large amount of bis-TMP is contained in the crude di-TMP. In Patent Document 7, the proportion of a content of bis-TMP to a content of di-TMP in the crude di-TMP is from 30 to 100%. Thus, when a large amount of tri-TMP or bis-TMP is contained in the raw material to be crystallized, these impurity compounds tend to be rapidly crystallized for a short period of time, so that growth of crystals of di-TMP tends to be inhibited, and a particle size of the crystals of di-TMP tends to become very fine. A creamy slurry containing a large amount of the fine crystals is hardly subjected to solid-liquid separation and therefore is difficult to handle especially in an industrial scale. Thus, it is not possible to obtain a high-purity di-TMP in an industrial manner.

CITATION LIST

Patent Literature

[Patent Document 1] U.S. Pat. No. 3,097,245
[Patent Document 2] JP 11-49708A
[Patent Document 3] WO 2009/057466A
[Patent Document 4] JP 47-30611A
[Patent Document 5] JP 49-133311A
[Patent Document 6] JP 2002-47231A
[Patent Document 7] JP 2002-47232A
[Patent Document 8] JP 2005-23067A
[Patent Document 9] JP 8-157401A

SUMMARY OF INVENTION

Technical Problem

The problem to be solved by the present invention is to provide a method for recovering di-TMP from a distillation still residue (crude di-TMP) obtained upon production of TMP which is free from the above-mentioned conventional problems and in which a high-purity di-TMP is produced in a simple, industrially useful and safe manner.

Solution to Problem

As a result of extensive and intensive researches regarding the methods for producing di-TMP which have suffered from the above conventional problems, the inventors have found that by strictly controlling conditions of re-distillation of a distillation still residue separated from purified trimethylolpropane to obtain a di-TMP-containing solution having reduced ratios of bis-TMP/di-TMP and tri-TMP/di-TMP, initiating crystallization of the di-TMP-containing solution with an organic solvent under specific conditions, and cooling the resulting reaction product solution, it is possible to efficiently recover di-TMP in a simple and convenient manner. The present invention has been accomplished on the basis of the above finding.

That is, the present invention relates to the following method for producing di-TMP.

1. A method for producing ditrimethylolpropane (di-TMP) by recovering the di-TMP from a reaction solution containing trimethylolpropane (TMP), the di-TMP, tritrimethylolpropane (tri-TMP) and bistrimethylolpropane (bis-TMP), which is produced by reacting n-butyl aldehyde and formaldehyde in the presence of a base catalyst, said method including the steps of:

(VI) distilling a distillation still residue obtained by distilling a crude TMP (A3) to separate purified TMP (A4) therefrom, wherein the crude TMP (A3) is obtained by distilling a reaction product-containing extract to remove a organic solvent (Y1) therefrom, wherein the reaction product-containing extract is extracted with an organic solvent (Y1) from a TMP-containing solution (A2),wherein the TMP-containing solution (A2) is obtained by distilling the reaction solution (A1) to remove unreacted formaldehyde therefrom; and (VII) subjecting the resulting di-TMP-containing solution to crystallization with an organic solvent (Y2) containing an aliphatic ketone, said method being carried out under the following conditions (1) and (2):

(1) a distillate obtained in the step (VI) contains the bis-TMP and the tri-TMP in amounts of 10 parts by mass or less and 5 parts by mass or less, respectively, on the basis of 100 parts by mass of the di-TMP; and (2) in the step (VII), the crystallization is initiated under pressure at a temperature exceeding a boiling point of the organic solvent (Y2) as measured under normal pressures, and the resulting crystallization product solution is cooled at a temperature drop rate of 2° C./min or less.

2. The method for producing ditrimethylolpropane as described in the above aspect 1, including the steps of:

(I) reacting n-butyl aldehyde and formaldehyde in the presence of the base catalyst to obtain the reaction solution (A1) containing the TMP, the di-TMP, and the bis-TMP and/or the tri-TMP as by-products;

(II) distilling the reaction solution (A1) to remove unreacted formaldehyde therefrom and obtain the TMP-containing solution (A2);

(III) subjecting the TMP-containing solution (A2) to extraction with the organic solvent (Y1) to separate a reaction product-containing extract therefrom;

(IV) distilling the extract obtained in the step (III) to remove the organic solvent (Y1) therefrom and obtain the crude TMP (A3);

(V) distilling the crude TMP (A3) to separate the purified TMP (A4) therefrom and obtain a di-TMP-containing solution (B1) from the distillation still residue;

(VI) further distilling the di-TMP-containing solution (B1) to separate a di-TMP-containing solution (B2) as a distillate therefrom; and (VII) subjecting the di-TMP-containing solution (B2) to crystallization with the organic solvent (Y2) containing an aliphatic ketone to obtain di-TMP (B3).

3. The method for producing ditrimethylolpropane as described in the above aspect 1 or 2, wherein the step (VI) is carried out using a distiller constructed from combination of a thin-film evaporator and a rectifying column, and a bottom pressure of the distiller upon further distilling the di-TMP-containing solution (B1) in the step (VI) is from 0.1 to 1.0 kPa.

4. The method for producing ditrimethylolpropane as described in any one of the above aspects 1 to 3, wherein a bottom temperature of the distiller upon further distilling the di-TMP-containing solution (B1) in the step (VI) is from 250 to 300° C.

5. The method for producing ditrimethylolpropane as described in any one of the above aspects 1 to 4, wherein a concentration of the tri-TMP in the di-TMP-containing solution (B2) supplied to the step (VII) is 5 parts by mass or less on the basis of 100 parts by mass of the di-TMP.

6. The method for producing ditrimethylolpropane as described in any one of the above aspects 1 to 5, wherein a concentration of the bis-TMP in the di-TMP-containing solution (B2) supplied to the step (VII) is 10 parts by mass or less on the basis of 100 parts by mass of the di-TMP.

7. The method for producing ditrimethylolpropane as described in any one of the above aspects 1 to 6, wherein the organic solvent (Y2) containing an aliphatic ketone which is used in the step (VII) is acetone.

8. The method for producing ditrimethylolpropane as described in any one of the above aspects 1 to 7, wherein in the step (VII), a mass ratio of the organic solvent (Y2) to the di-TMP-containing solution (B2) [organic solvent (Y2)/di-TMP-containing solution (B2)] is from 0.5 to 20.

9. The method for producing ditrimethylolpropane as described in any one of the above aspects 1 to 8, wherein a temperature upon initiation of the crystallization in the step (VII) is from 70 to 90° C.

10. The method for producing ditrimethylolpropane as described in any one of the above aspects 1 to 9, wherein a pressure upon initiation of the crystallization in the step (VII) is from 0.11 to 0.3 MPa.

11. The method for producing ditrimethylolpropane as described in any one of the above aspects 1 to 10, wherein in the step (VII), the crystallization initiation temperature is held for a time period of from 0.1 to 5 hours.

12. The method for producing ditrimethylolpropane as described in any one of the above aspects 1 to 11, wherein a temperature upon termination of the crystallization in the step (VII) is from 40 to 20° C.

13. The method for producing ditrimethylolpropane as described in any one of the above aspects 1 to 12, wherein a pressure upon termination of the crystallization in the step (VII) is from 100 to 20 kPa.

14. The method for producing ditrimethylolpropane as described in any one of the above aspects 1 to 13, wherein the organic solvent (Y2) vaporized in the step (VII) is cooled and fed back to the crystallization system to remove heat generated upon the crystallization.

Advantageous Effects of Invention

According to the present invention, it is possible to produce a high-purity di-TMP from crude di-TMP as a still residue separated upon production of TMP with a high recovery rate in a simple, industrially useful manner.

In addition, in the present invention, any harmful solvent, in particular, 1,4-dioxane, is not used, so that the di-TMP can be produced with a high safety.

DESCRIPTION OF EMBODIMENTS

The method for producing ditrimethylolpropane (di-TMP) by recovering the di-TMP from a reaction solution containing trimethylolpropane (TMP), the di-TMP, tritrimethylolpropane (tri-TMP) and bistrimethylolpropane (bis-TMP), which is produced by reacting n-butyl aldehyde and formaldehyde in the presence of a base catalyst, according to the present invention, is characterized by including the steps of:

(VI) distilling a distillation still residue obtained by distilling a crude TMP (A3) to separate purified TMP (A4) therefrom, wherein the crude TMP (A3) is obtained by distilling a reaction product-containing extract to remove a organic solvent (Y1) therefrom, wherein the reaction product-containing extract is extracted with an organic solvent (Y1) from a TMP-containing solution (A2), wherein the TMP-containing solution (A2) is obtained by distilling the reaction solution (A1) to remove unreacted formaldehyde therefrom; and (VII) subjecting the resulting di-TMP-containing solution to crystallization with an organic solvent (Y2) containing an aliphatic ketone, said method being carried out under the following conditions (1) and (2):

(1) a distillate obtained in the step (VI) contains the bis-TMP and the tri-TMP in amounts of 10 parts by mass or less and 5 parts by mass or less, respectively, on the basis of 100 parts by mass of the di-TMP; and (2) in the step (VII), the crystallization is initiated under pressure at a temperature exceeding a boiling point of the organic solvent (Y2) as measured under normal pressures, and the resulting crystallization product solution is cooled at a temperature drop rate of 2° C./min or less.

The method for producing the di-TMP according to the present invention preferably includes the following steps.

Step (I): reacting n-butyl aldehyde (NBD) and formaldehyde in the presence of the base catalyst to obtain the reaction solution (A1) containing the TMP, the di-TMP, and the bis-TMP and/or the tri-TMP as by-products.

Step (II): distilling the reaction solution (A1) to remove unreacted formaldehyde therefrom and obtain the TMP-containing solution (A2).

Step (III): subjecting the TMP-containing solution (A2) to extraction with the organic solvent (Y1) to separate a reaction product-containing extract therefrom.

Step (IV): distilling the extract obtained in the step (III) to remove the organic solvent (Y1) therefrom and obtain the crude TMP (A3).

Step (V): distilling the crude TMP (A3) to separate the purified TMP (A4) therefrom and obtain a di-TMP-containing solution (B1) from the distillation still residue.

Step (VI): further distilling the di-TMP-containing solution (B1) to separate a di-TMP-containing solution (B2) as a distillate therefrom.

Step (VII): subjecting the di-TMP-containing solution (B2) to crystallization with the organic solvent (Y2) to obtain di-TMP (B3).

Meanwhile, as the organic solvent (Y1), there is preferably used at least one organic solvent selected from the group consisting of aliphatic esters, aliphatic ketones, aliphatic alcohols and aliphatic aldehydes. As the organic solvent (Y2), there may be used aliphatic ketones.

The steps (I) to (V) are ordinary steps generally conducted for production of TMP. The ditrimethylolpropane (di-TMP) as the aimed product of the present invention is represented by the following chemical formula:

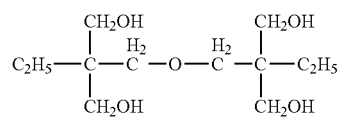

The reaction solution (A1) obtained in the step (I) by reacting n-butyl aldehyde (NBD) and formaldehyde in the presence of the base catalyst contains not only the TMP and the di-TMP, but also the bis-TMP, the tri-TMP and/or 2-ethyl-2-propenal (ECR) as by-products.

The bistrimethylolpropane (bis-TMP) by-produced as a high-boiling substance is represented by the following chemical formula.

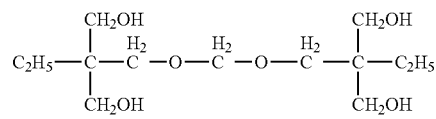

In the present invention, the reaction solution containing TMP, di-TMP, tri-TMP or the like which is produced by reacting NBD, formaldehyde and the base in the step (I) is subjected to distillation in the step (II) to remove remaining unreacted formaldehyde therefrom. Then, in the step (III), the obtained reaction product is extracted with the organic solvent (Y1). Further, in the step (IV), the organic solvent (Y1) used for the extraction is removed by distillation from the resulting extract. The resulting crude TMP is distilled in the step (V) to separate TMP as a distillate therefrom. In the step (VI), the resulting distillation still residue is further distilled. The resulting distillate is subjected to crystallization with the organic solvent (Y2) in the step (VII) to produce the di-TMP. The distillation still residue (B1; crude di-TMP) obtained in the step (V) preferably has the following composition.

| | |
|---|---|
| Trimethylolpropane (TMP) | From 1 to 30% by mass |
| Ditrimethylolpropane (di-TMP) | From 50 to 70% by mass |
| Bistrimethylolpropane (bis-TMP) | From 1 to 30% by mass |
| Tritrimethylolpropane (tri-TMP) | From 0.5 to 20% by mass |

Namely, in the present invention, in order to increase an amount of di-TMP recovered, it is preferred to first recover 2-ethyl-2-propenal (ECR) and then produce di-TMP from TMP, ECR and formaldehyde according to the following reaction formula as shown in the method described in Patent Document 3.

Meanwhile, formic acid (HCOOH) is produced in the reaction. However, the formic acid thus produced is reacted with the base catalyst to form a formate.

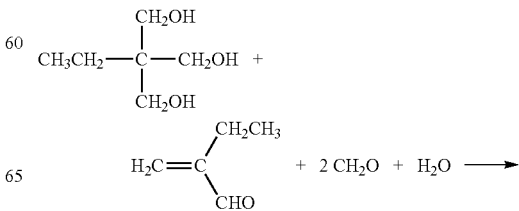

-continued

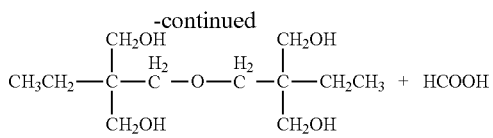

When the amount of di-TMP recovered is increased by the method described in Patent Document 3, the method includes three steps, i.e., a step (I-1) of reacting NBD and formaldehyde (F1) in the presence of a base catalyst (C1); a step (I-2) of distilling the resulting reaction mixture solution to recover 2-ethyl-2-propenal (ECR) therefrom; and a step (I-3) of adding ECR and formaldehyde (F2), or ECR, formaldehyde (F2) and a base catalyst (C2), to the distillation residue solution to allow the production reaction of di-TMP to proceed.

When not adopting the method described in Patent Document 3 in which the bis-TMP/di-TMP ratio is reduced, for example, when adopting the method described in Patent Document 7 in which the bis-TMP/di-TMP ratio is not improved, the content of di-TMP in the distillation still residue obtained in the step (V) is less than 50% by mass. If the content of di-TMP in the distillation still residue is less than 50% by mass, the contents of bis-TMP and tri-TMP in the distillate obtained in the step (VI) are hardly controlled to 10 parts by mass or less and 5 parts by mass or less, respectively, on the basis of 100 parts by mass of di-TMP. As a result, it will be difficult to finally obtain a high-purity di-TMP.

The NBD used as the raw material in the method for producing di-TMP according to the present invention may be an ordinary commercially available NBD. The commercially available NBD may be further purified by distillation or the like, if required, upon use.

The formaldehyde as the other raw material for production of di-TMP may be in the form of either a formaldehyde aqueous solution or solid paraformaldehyde. The formaldehyde aqueous solution usually contains several mass percents of methanol as a stabilizer, and may also be subjected to distillation or the like, if required, to remove the methanol. The formaldehyde is supplied to the step (I-1) and the step (I-3). In the present invention, the formaldehyde supplied to the step (I-1) is referred to as "F1" whereas the formaldehyde supplied to the step (I-3) is referred to as "F2".

The base catalyst used in the present invention may be formed from either an inorganic base or an organic base. Examples of the inorganic base include hydroxides and carbonates of alkali metals or alkali earth metals. Specific examples of the inorganic base include sodium hydroxide, potassium hydroxide, calcium hydroxide, lithium hydroxide, sodium carbonate, potassium carbonate, calcium carbonate and lithium carbonate. Among these inorganic bases, preferred are carbonates and/or hydrogen carbonates of alkali metals or alkali earth metals. In particular, base catalysts containing an alkali metal carbonate as a main component are more preferred. From the industrial viewpoints, sodium salts are generally used as the base catalyst.

Examples of the organic base used in the present invention include aliphatic amine compounds, in particular, tertiary amines. Specific examples of the tertiary amines include trimethylamine, triethylamine, diethylmethylamine, dimethylethylamine, triisopropylamine and tributylamine.

Similarly to the formaldehyde, the base catalyst supplied to the step (I-1) is referred to as "C1" whereas the base catalyst supplied to the step (I-3) is referred to as "C2". However, the C2 may not be supplied to the step (I-3) in some cases since the distillation residue solution obtained in the step (I-2) already contains the base catalyst.

As the base catalyst, the above-mentioned inorganic bases and organic bases may be used not only singly but also in combination of any two or more thereof, for example, triethylamine may be used as C1, and sodium hydroxide may be used as C2. Alternatively, a plurality of the inorganic bases or organic bases may be continuously used.

When using the base catalyst containing an alkali metal carbonate as a main component, the carbonate is consumed in the reaction to form a hydrogen carbonate, and the hydrogen carbonate produced in the reaction is converted into a carbonate by the action of heat and the like which is then consumed again in the reaction. The base catalyst containing an alkali metal carbonate as a main component may be those carbonates generally commercially available as industrial reagents or in the form of a mixture of the carbonate with a hydrogen carbonate. Also, there may be used carbonates produced using a hydrogen carbonate obtained by oxidation or hydrolysis of a formate as a raw material, or a mixture of the carbonate with a hydrogen carbonate.

The reaction of the step (I-1) may be conducted by various methods such as, for example, a method of adding dropwise NBD and the base catalyst (C1) in parallel into the formaldehyde (F1) aqueous solution, and a method of first mixing the F1 aqueous solution and C1, and adding dropwise NBD into the resulting mixture at a constant velocity.

When adding dropwise NBD and C1 in parallel into the F1 aqueous solution, each of NBD and C1 is preferably added over a time period of from 1 to 600 minutes, and more preferably from 10 to 360 minutes. When adding dropwise NBD into the mixture of the F1 aqueous solution and C1, NBD may be added over the same time period as above. The dropping time is 600 minutes or shorter in view of improved production efficiency.

The amount of F1 used is from 2.0 to 3.5 mol and preferably from 2.0 to 3.0 mol per 1 mol of NBD. When the amount of F1 used is 2.0 mol or more, the production reaction of di-TMP is promoted, and side reactions between molecules of NBD as the raw material and a secondary production reaction of bis-TMP are hardly caused. Also, when the amount of F1 used is 3.5 mol or less, the amount of ECR recovered by distillation is increased, and the amount of di-TMP produced is increased.

The equivalent amount of C1 is from 0.5 to 1.5 equivalents per 1.0 mol of NBD. When the equivalent amount of C1 is 0.5 equivalents or more, the production reaction of the aimed di-TMP is promoted, and side reactions between molecules of NBD as the raw material and the like are hardly caused.

The amount of C1 used may vary depending upon the kind of base used and the reaction conditions such as, reaction temperature and reaction time. For example, when using a strong base such as sodium hydroxide, the base added is immediately reacted. For this reason, the amount of C1 used is preferably close to 0.5 equivalents as a lower limit thereof, and the use of a large amount of C1 is undesirable because of occurrence of side reactions. On the contrary, when using a weak base such as sodium carbonate having a low reactivity, the amount of C1 used is preferably close to 1.5 equivalents as an upper limit thereof.

The reaction temperature in the step (I-1) is preferably from 45 to 120° C. and more preferably from 60 to 110° C. The mixture obtained by adding NBD or C1 into the F1 aqueous solution may be heated for a time period of from 1 to 300 minutes in the temperature range of from 45 to 120° C. to further promote the reaction. In this case, in order to maintain an inside of the reaction system at the predetermined reaction temperature, the reaction system may be pressurized by introducing an inert gas such as a nitrogen gas thereinto.

In the step (I-2), the reaction solution obtained in the step (I-1) is subjected to distillation to recover 2-ethyl-2-propanal (ECR) therefrom. ECR produced within the reaction system may be separated and recovered in the course of the reaction of the step (I-2) while continuing the reaction in parallel with the reaction of the step (I-1) or after completion of the reaction of the step (I-2).

The separation and recovery of ECR may be readily carried out by distillation under reduced pressure, under normal pressures or under application of pressure. Although it is desirable to recover a whole amount of ECR, a part of ECR may remain within the reaction system.

The distillation temperature is from 45 to 120° C., and preferably from 90 to 110° C. when conducted under atmospheric pressure. The amount of ECR recovered by the distillation is preferably from 0.05 to 0.5 mol, more preferably from 0.06 to 0.45 mol and still more preferably from 0.1 to 0.35 mol per 1.0 mol of NBD as the raw material. When the reaction of the next step (I-3) is carried out while controlling the amount of ECR recovered to the above-specified range, the amount of di-TMP produced is increased, and di-TMP can be therefore produced with a high efficiency.

When recovering ECR by distillation, ECR undergoes azeotropy with water. Therefore, the distillate produced upon distillative recovery of ECR contains water. The distillate when allowed to stand is immediately separated into an oil phase (ECR-containing phase) and a water phase. The amount of water entrained in ECR distilled is preferably from 0.01 to 20 times and more preferably from 0.1 to 2.0 times a mass of ECR distilled.

An ordinary industrial formaldehyde aqueous solution contains methanol. The methanol is distilled off together with ECR. At this time, when controlling the amount of water distilled off together with ECR and entrained in ECR to 0.01 times or more the mass of ECR distilled, the methanol is dissolved in the water phase and prevented from remaining in the oil phase, so that no production of by-products by the reaction between methanol and ECR can be prevented. As a matter of course, these problems may be avoided by using formaldehyde or paraformaldehyde containing no methanol as the raw material. However, from the industrial viewpoints such as a high recovery efficiency, the recovery of ECR together with water is preferred in order to recover a sufficient amount of ECR. To avoid a prolonged distillation time in the step (II), the amount of water distilled together with ECR and entrained in ECR is controlled to 20 times or less the mass of ECR distilled.

The above distillate contains not only ECR, but also water and organic components such as methanol. The distillate may be used as such in the step (I-3). If required, the distillate may be subjected to purification treatment such as distillation, and then subjected to the reaction with formaldehyde in the step (I-3).

The distillate that is separated into an oil phase and a water phase may be added as such to the distillation residue solution or may be added thereto after stirring and mixing, or the respective phases isolated from each other may be individually added thereto. Further, after adding one of the oil phase and the water phase, the remaining one may be then added.

The distillation residue solution contains not only TMP and high-boiling point substances produced in the step (I-1), but also unreacted formaldehyde, water derived from the formaldehyde aqueous solution as the raw material and water by-produced in the crossed Cannizzaro reaction. Thus, in the distillation residue solution, there may be present not only a large amount of TMP as one of the aimed products but also intermediate products produced not after completion of the reaction but partially in the course of the reaction. In order to convert the intermediate products into TMP, the distillation residue solution obtained after the distillative recovery is preferably heated at a temperature of from 45 to 120° C. for a time period of from 1 to 300 minutes to complete the reaction.

In the step (I-3), ECR recovered and formaldehyde (F2) together with or without a base catalyst (C2) are added to the distillation residue solution containing TMP which is obtained after recovering ECR in the step (I-2), thereby allowing the production reaction of di-TMP to proceed.

The amount of F2 added in the step (I-3) is determined from a whole amount of formaldehyde used at a predetermined proportion on the basis of NBD as the raw material, and a remaining amount of formaldehyde which is calculated by subtracting the amount of formaldehyde added in the step (I-1) from the whole amount of formaldehyde is added as F2 in the step (I-3).

More specifically, the amount of F2 added is adjusted such that a total amount of F1 and F2 is from 3.0 to 4.5 mol, preferably from 3.0 to 4.0 mol and more preferably from 3.1 to 3.5 mol per 1.0 mol of n-butyl aldehyde as the raw material. When the total amount of F1 and F2 is controlled to 3.0 mol or more, the amount of di-TMP produced is increased to a theoretical amount of di-TMP obtained in the production reaction or larger, so that the amount of by-products produced is reduced. When the total amount of F1 and F2 is controlled to 4.5 mol or less, the ratio of the amount of di-TMP produced to the amount of TMP produced is increased, so that the amount of bis-TMP produced as a by-product is decreased.

The amount of the base catalyst (C2) added is adjusted such that a total amount of the base catalyst (C1) and the base catalyst (C2) is from 1.0 to 2.5 equivalents and preferably 1.0 to 1.5 equivalents per 1.0 mol of n-butyl formaldehyde as the raw material. Thus, the base catalyst is used as C2 in the step (I-1) and a remaining amount of the base catalyst is used as C2 in the step (I-3) such that the total amount of the base catalysts used falls within the above specified-range.

For example, when a divalent base (2.0 equivalents) such as sodium carbonate and calcium hydroxide is used as C1 and C2, the total amount of C1 and C2 is adjusted to from 1.0 to 2.5 equivalents (0.5 to 1.25 mol) per 1.0 mol of NBD. When the total amount of C1 and C2 is controlled to 1.0 equivalent or more, a large amount of the raw materials are prevented from remaining unreacted, so that side reactions of the unreacted raw materials are hardly caused. When the total amount of C1 and C2 is controlled to 2.5 equivalents or less, the use of a large amount of an acid for neutralizing an excess amount of the base can be prevented.

In the method of adding dropwise ECR recovered by distillation and F2 together with or without C2 to the distillation residue solution obtained after recovering ECR in the step (I-2), these components are continuously added dropwise over a time period of from 1 to 300 minutes for each component by sequential dropwise addition of the respective components, simultaneous in-parallel dropwise addition of the components, or the like. In the simultaneous in-parallel dropwise addition of the components, the dropwise addition of any of the components may be first terminated.

The reaction temperature used in the step (I-3) may vary depending upon the kind of base used, and is preferably from 45 to 120° C. and more preferably from 60 to 120° C. In particular, when using a carbonate as the base catalyst, it is required to maintain the reaction temperature sufficient to ensure conversion of a hydrogen carbonate produced in the reaction into a carbonate. From this viewpoint, the reaction temperature is preferably from 60 to 120° C. and more preferably from 80 to 120° C. In the above reaction, in order to maintain an inside of the reaction system at the predetermined reaction temperature, the reaction system may be pressurized by introducing an inert gas such as a nitrogen gas thereinto.

In the case where ECR as the raw material is not completely consumed at the time at which the addition of ECR recovered by the distillation and F2 together with or without C2 to the distillation residue solution obtained after recovering ECR is terminated, the reaction system is preferably further heated to complete the reaction. The reaction temperature used in such a case may vary depending upon the kind of base used, and is preferably from 45 to 120° C. and more preferably from 60 to 120° C. In particular, when using a carbonate as C2, it is required to maintain the reaction temperature sufficient to ensure conversion of a hydrogen carbonate produced in the reaction into a carbonate. From this viewpoint, the reaction temperature is preferably from 60 to 120° C. and more preferably from 80 to 120° C. In the above reaction, in order to maintain an inside of the reaction system at the predetermined reaction temperature, the reaction system may also be pressurized by introducing an inert gas such as a nitrogen gas thereinto. The heating time required to complete the reaction is preferably from 1 to 180 minutes and more preferably from 30 to 120 minutes. In order to avoid undesirable coloring of the reaction solution, the heating time is 180 minutes or shorter.

The reactions of the step (I-1) and the step (I-3) may be carried out in respective separate reactors under the conditions identical to or different from each other, or may be sequentially carried out in the same reactor. For example, when the reactions are carried out in the respective separate reactors, triethylamine may be used as C1 in the step (I-1), and sodium hydroxide may be used as C2 in the subsequent step (I-3).

As described above, when the step (I) of obtaining the reaction solution (A1) containing TMP and di-TMP as well as bis-TMP and/or tri-TMP as by products by reacting NBD and formaldehyde in the presence of the base catalyst is carried out through the steps (I-1) to (I-3), it is possible to obtain the reaction solution (A1) having a high di-TMP concentration.

The step (II) of distilling the reaction solution (A1) to remove unreacted formaldehyde therefrom and obtain the TMP-containing solution (A2); the step (III) of subjecting the TMP-containing solution (A2) to extraction with the organic solvent (Y1); the step (IV) of distilling the resulting extract to remove the organic solvent (Y1) therefrom and obtain the crude TMP (A3); and the step (V) of distilling the crude TMP (A3) to separate the purified TMP (A4) therefrom and obtain the di-TMP-containing solution (B1) from the distillation still residue are ordinary procedures generally conducted for purification of TMP, and may be carried out by the methods described in Patent Documents 2 and 4 to 6 as the background arts, or the like.

In the step (II), for example, an excess of the alkali remaining in the reaction solution (A1) is neutralized with formic acid, and then the resulting reaction solution is subjected to distillation under application of a pressure of from 0.15 to 0.35 MPa to remove the residual formaldehyde therefrom and obtain the TMP-containing solution (A2).

All of the reactions and operations of the steps (I) and (II) may be respectively carried out in a dedicated apparatus provided for each of the reactions and operations, or may be carried out using a single apparatus or a plurality of apparatuses which are ready for the corresponding reactions and operations.

In the step (III), the TMP-containing solution (A2) is subjected to extraction with the organic solvent (Y1) to extract the reaction products contained in the TMP-containing solution (A2) (such as TMP, di-TMP, bis-TMP and tri-TMP), thereby obtaining a TMP extract containing substantially no formate. Examples of the organic solvent (Y1) used in the step (III) include aliphatic esters such as ethyl acetate and butyl acetate; aliphatic ketones such as methyl ethyl ketone, methyl isobutyl ketone and diisopropyl ketone; aliphatic alcohols such as isobutanol, amyl alcohol, hexyl alcohol and cyclohexanol; and aliphatic aldehydes such as isobutyl aldehyde and n-butyl aldehyde (NBD). These organic solvents may be used in the form of a mixed extractant constituted from any two or more thereof. Among these organic solvents, NBD is especially preferred because it is used as the raw material.

The amount of the organic solvent (Y1) used and the extraction conditions upon using the organic solvent (Y1) are not particularly limited. The extraction is usually carried out at a temperature of from 5 to 55° C. using the organic solvent in an amount of from 0.5 to 5 times the mass of the TMP-containing solution (A2).

In the step (IV), the organic solvent (Y1) is distilled off from the TMP extract obtained in the step (III). The pressure on the bottom side may vary depending upon the organic solvent used, and is from about 6.7 to about 101.3 kPa.

In the step (V), the crude TMP (A3) obtained by distilling off the organic solvent (Y1) is further subjected to distillation under a high vacuum of from 0.1 to 5 kPa to obtain the purified TMP (A4), thereby separating the di-TMP-containing solution (B1) from the distillation still residue.

In the step (VI), the di-TMP-containing solution (B1) is further subjected to distillation to obtain the di-TMP-containing solution (B2) as a distillate which is subsequently used as the raw material for the crystallization. The by-products such as bis-TMP and tri-TMP were separated from the distillation still residue, thereby obtaining the di-TMP-containing solution (B2) containing less amounts of bis-TMP and tri-TMP.

In the step (VI), the pressure on the bottom side is from 0.1 to 1.0 kPa, preferably from 0.15 to 0.8 kPa and more preferably from 0.2 to 0.5 kPa. When the bottom-side pressure is 1.0 kPa or less, the recovery rate of di-TMP as the aimed product can be enhanced. When the bottom-side pressure is 0.1 kPa or more, there can be attained the industrial advantages such as (1) suppressing entrainment of the bis-TMP and tri-TMP in a distillate to thereby control concentrations of the bis-TMP and tri-TMP in the distillate to the values suitable for supplying the distillate to the step (VII), and (2) requiring no expensive high-vacuum generating facility. The vacuum-generating method is not particularly limited.

When obtaining the di-TMP-containing solution (B2) by distillation, the temperature on the bottom side is from 250 to 300° C. and preferably from 250 to 280° C. When the bottom-side temperature is 250° C. or higher, the recovery rate of di-TMP having a high boiling point can be enhanced. When the bottom-side temperature is 300° C. or lower, the bottom-side pressure can be prevented from increasing owing to a large amount of low-boiling components produced by thermal decomposition of the di-TMP-containing solution (B2), or the recovery rate of di-TMP as the aimed product can be prevented from decreasing.

As the distillation apparatus, there is preferably used a rectifying column having a theoretical plate number of from about 1 to about 10. To achieve the above bottom-side pressure, a low differential pressure packing column may be suitably used. As the evaporator, there may be used ordinary multipipe heat exchangers and plate-type heat exchangers. In particular, a thin-film evaporator is more suitably used. In order to separate di-TMP from bis-TMP and tri-TMP, it is desirable to use combination of the rectifying column and the thin-film evaporator. The heating medium used in the distillation is not particularly limited.

In the step (VI), the concentration of bis-TMP in the di-TMP-containing solution (B2) is 10 parts by mass or less, preferably 7 parts by mass or less and more preferably 5 parts by mass or less on the basis of 100 parts by mass of di-TMP. When the concentration of bis-TMP in the di-TMP-containing solution (B2) is 10 parts by mass or less, promotion of supersaturation phenomenon upon the crystallization can be prevented, and precipitation of crystals at an extremely low temperature can be prevented. The crystal particles rapidly precipitated at a low temperature have a very fine particle size, which therefore results in preparation of not a good slurry but a creamy slurry. Even though such a creamy slurry is subjected to solid-liquid separation, it is not possible to obtain a high-purity di-TMP, and troubles such as clogging of a filter material tend to occur.

The concentration of tri-TMP in the di-TMP-containing solution (B2) is 5 parts by mass or less, preferably 4 parts by mass or less and more preferably 3 parts by mass or less on the basis of 100 parts by mass of di-TMP. When the concentration of tri-TMP in the di-TMP-containing solution (B2) is 5 parts by mass or less, not only reduction in purity of di-TMP obtained by subjecting the solution to solid-liquid separation and increase in a phthalic acid resin color as a degree of coloring thereof can be avoided, but also the crystals are prevented from being solidified into block-shaped mass and are easy to handle upon an industrial use.

In the step (VII), the organic solvent (Y2) is added to the di-TMP-containing solution (B2) obtained by the distillation in the step (VI), and the resulting precipitated crystals are subjected to filtration or centrifugal separation to recover a high-purity di-TMP. The apparatus used in the crystallization is not particularly limited, and a stirring vessel may be generally used.

As the organic solvent (Y2) added upon the crystallization, there may be used aliphatic ketones. Among the aliphatic ketones, more preferred are acetone and methyl ethyl ketone, and most preferred is acetone. These organic solvents may be ordinary industrial products and can be used as such in the step (VII) without need of any further purification treatment.

The organic solvent (Y2) is used in the step (VII) in an amount of from 0.5 to 20 times, preferably from 0.8 to 10 times and especially preferably from 1 to 3 times the mass of the di-TMP-containing solution (B1) and/or the di-TMP-containing solution (B2) as a distillate of the solution (B1). When the amount of the organic solvent (Y2) used is 0.5 time or more the mass of the solution (B1) and/or the solution (B2), precipitation of impurities such as TMP together with di-TMP can be prevented, so that the purity of crystals of di-TMP is not lowered. When the amount of the organic solvent (Y2) used is 20 times or less the mass of the solution (B1) and/or the solution (B2), deterioration in yield of crystals of di-TMP and failure to obtain crystals of di-TMP can be prevented. In addition, occurrence of excessive solvent recovery load can be avoided, which will become industrially advantageous.

In the step (VII), the organic solvent (Y2) is added to the di-TMP-containing solution (B2) obtained by the distillation in the step (VI), and the resulting solution is heated while stirring and then cooled. The time at which cooling of the solution is initiated is regarded as the time of "initiation of crystallization". In the present invention, the crystallization initiation temperature is adjusted to a temperature exceeding a boiling point of the solvent as measured under normal pressures. When the concentration of di-TMP in the di-TMP-containing solution (B2) is 55% by mass or more, it is not possible to completely dissolve di-TMP therein under the conditions as described in Patent Document 8, so that no high-purity di-TMP can be obtained. However, in the method of the present invention, the crystallization of di-TMP is initiated under pressure at a temperature exceeding a boiling point of the solvent as measured under normal pressures. As a result, even though the concentration of di-TMP in the raw material for the crystallization is high, it is possible to obtain a high-purity di-TMP. Meanwhile, the crystallization initiation pressure is preferably from 0.11 to 0.3 MPa.

When using acetone as the organic solvent (Y2), the crystallization initiation temperature is from 65 to 90° C., preferably from 70 to 90° C. and more preferably from 75 to 85° C. When the crystallization initiation temperature is raised to 90° C. or higher, the crystallization initiation pressure tends to exceed 0.2 MPa. The crystallization vessel used under such a high pressure should conform to regulations of the High Pressure Gas Safety Act. Many limitations concerning installation of such an apparatus are prescribed in the Act, and therefore special care must be taken when the crystallization vessel is industrially installed. Under these circumstances, it is not necessary to raise the crystallization initiation temperature to 90° C. or higher.

In the step (VII), the cooling rate until reaching the temperature at which the crystallization is terminated is lowered to increase a particle size of the resulting crystals and improve a handling property thereof. The cooling rate is 2° C./min or less, and preferably 1.5° C./min or less. When the cooling rate is 2° C./min or less, the obtained crystals have a small particle size, and are therefore free from deterioration in solid-liquid separation capability, resulting in industrial easiness of handling.

In order to remove heat generated upon the crystallization, it is generally known that the reactor is cooled by using a jacket, an internal coil or the like. Also, there is known a method of vaporizing the organic solvent (Y2) by gradually reducing an inside pressure of the reactor to cool the reactor by the heat of vaporization. The vapor of the organic solvent generated upon reducing an inside pressure of the reactor may be cooled and then fed back to the crystallization system. In the method utilizing the heat of vaporization, it is possible to avoid deterioration in heat removal efficiency owing deposition (scaling) of the crystals onto a transfer surface of the jacket or the internal coil. The cooling device used for cooling the vapor of the organic solvent (Y2) is not particularly limited, and may be an ordinary multipipe heat exchanger and the like.

When the vapor of the organic solvent (Y2) is cooled and then fed back to the crystallization system in order to cool the reactor upon the crystallization, the reactor can be more efficiently cooled by reducing an inside pressure thereof. The operating pressure is adjusted to such a pressure that a boiling point of the solvent corresponds to an aimed temperature upon termination of the crystallization, and more specifically is to be controlled to a pressure of from 100 to 20 kPa, preferably from 80 to 25 kPa and more preferably from 50 to 26 kPa. When the operating pressure is 20 kPa or more, the organic solvent (Y2) is readily cooled and free from occurrence of loss owing to flowing into the side of a vacuum generator, which will become industrially advantageous. When the operating pressure is 100 kPa or less, the organic solvent (Y2) can be vaporized to utilize absorption of heat by the vaporization, and further advantages such as good cooling efficiency and prevention of scaling can be attained as described above.

When the temperature upon termination of the crystallization is becomes low, a solubility of di-TMP in the organic solvent (Y2) is reduced and a recovery rate of the crystals is increased. The crystallization termination temperature is usually from 50 to 20° C., preferably from 40 to 25° C. and more preferably from 35 to 30° C. When the crystallization termination temperature is 20° C. or higher, impurities such as bis-TMP and tri-TMP are prevented from being precipitated so that the product with a high purity can be obtained. In order to enhance the recovery efficiency when cooling, the pressure of the crystallization system may be reduced during the crystallization to lower the temperature such that the solubility of di-TMP in the organic solvent (Y2) is decreased. Meanwhile, in order to maintain a recovery rate of di-TMP, the crystallization termination temperature is preferably held for 1 hour or longer after reaching the temperature as aimed.

In the step (VII), the following procedures are preferably conducted. That is, the raw material for the crystallization and the organic solvent (Y2) are charged into a pressurizable crystallization vessel, and after replacing an inside atmosphere of the vessel with an inert gas, the contents of the vessel are heated to a predetermined temperature while stirring. After reaching the predetermined temperature and pressure, the contents of the vessel are held at the temperature and pressure for 0.1 to 5 hours, and then cooled at a predetermined temperature drop rate to confirm a temperature at which precipitation of crystals is initiated (i.e., a temperature at which the temperature rise is initiated by heat of crystallization), and further cooled until reaching a predetermined crystallization retention temperature. After the elapse of a predetermined crystallization retention time, the pressure in the crystallization vessel is dropped to recover a slurry.

The slurry obtained in the step (VII) is subjected to filtration or centrifugal separation to separate the crystals of di-TMP therefrom. The thus obtained crystals are washed with the organic solvent (Y2) and then dried, thereby obtaining a high-purity di-TMP.

Meanwhile, a filtrate produced in the crystallization step or the solvent recovered by distillation of the washing solution of the crystals may be used again as the solvent (Y2) for the crystallization similarly to the solvent recovered upon drying of di-TMP.

EXAMPLES

The present invention will be described in more detail below by referring to the following examples. It should be noted, however, that the following examples are only illustrative and not intended to limit the invention thereto.

The raw materials used in the following Examples were commercially available reagents and the like. More specifically, NBD as a guaranteed reagent available from Sigma-Aldrich Corp., an industrial 40% by mass formaldehyde aqueous solution (methanol content: 3% by mass) available from Mitsubishi Gas Chemical Co., Inc., and sodium carbonate as a guaranteed reagent available from Wako Pure Chemical Industries, Ltd., were used as the respective raw materials.

The analysis was conducted by gas chromatography (GC) using a dilute solution prepared by diluting a sample and an internal standard substance with an acetone solvent.

[Conditions of Gas Chromatography]
  Apparatus: "HP-5890" (available from Agilent Technologies Corp.)
  Column used: "DB-1" (available from Agilent Technologies Corp.)
  Analyzing Conditions: Injection temperature: 250° C.
  Detector temperature: 250° C.
  Column Temperature: Held at 60° C. for 6 minutes→Raised to 250° C. at a rate of 7° C./min→Held at 250° C. for 20 minutes
  Detector: Flame ionization detector (FID)

Meanwhile, in the following Examples, "%" and "ppm" respectively indicate the values on a mass basis unless otherwise specified.

The purity of a sample was the value calculated by an area percentage method in which the sample was subjected to silylation and then directly charged into a gas chromatograph. The silylation was conducted by the following method using the same gas chromatography conditions as described above.

Silylation: 0.5 mL of a silylating agent (N,O-bis(trimethylsilyl)trifluoroacetamide) and 1 mL of pyridine were added to 25 mg of a sample, and the resulting mixture was reacted on a sand bath under heating at 95° C. for 2 hours.

Also, the degree of coloring is represented by a phthalic acid resin color as determined by a phthalic acid resinification testing method. That is, 5.4 g of phthalic anhydride crystals (JIS K 4128) and 3 g of di-TMP crystals were weighed and charged into a test tube (18 mm in diameter and 165 mm in whole length as prescribed in JIS R 3503) in which a small amount of glass boiling stones were filled, and the thus filled test tube was placed in an aluminum block heater previously heated to 265° C. The test tube was heated in the heater over 5 minutes while sometimes taking the test tube from the heater to shake and mix the contents thereof. Then, the test tube was taken out from the heater and allowed to stand upright in parallel with another test tube filled with a colorimetric standard solution at about 20° C. in front of a white background. The test tubes were subjected to calorimetric analysis by viewing therethrough from their front side under irradiation with diffused daylight or light identical to or stronger than the daylight. The colorimetric standard solution was formulated as follows. That is, a cobalt (II) chloride colorimetric stock solution, an iron (III) chloride colorimetric stock solution and a copper (II) sulfate colorimetric stock solution were mixed with each other at a volume ratio of 2:5:1, and then the resulting mixed stock solution was diluted with water at a predetermined volume ratio. For example, the colorimetric standard solution formulated by diluting the mixed stock solution with water at a volume ratio of 1:9 was referred to as a "colorimetric standard solution No. 1", and the colorimetric standard solution formulated by diluting the mixed stock solution with water at a volume ratio of 9:1 was referred to as a "colorimetric standard solution No. 9".

Production Example 1

<Production of Di-TMP-Containing Solution (B1)>

First, the reaction solution (A1) used in the step (I) was produced according to the method described in Example 1 of Patent Document 2.

Step (I-1): A 1000 mL four-necked flask equipped with a reflux condenser, a thermometer and two dropping funnels was charged with 208.7 g of a 40% formaldehyde (F1) aqueous solution (formaldehyde content: 2.8 mol; 82% on the basis of a whole amount of formaldehyde used), followed by heating the formaldehyde aqueous solution to 72° C. Thereafter, whole amounts of 72 g (1.0 mol) of NBD and 263 g (0.53 mol=1.06 equivalents) of a 21% sodium carbonate aqueous solution were added dropwise to the flask while gradually heating from the dropping funnels, and the contents of the flask were further heated at 80° C. for 2 minutes to obtain a reaction mixture solution.

Step (I-2): The reaction mixture solution obtained in the step (I-1) was heated to 100° C. and subjected to distillation for 30 minutes to recover ECR therefrom. The solution recovered by distillation contained 22 mL of an oil phase (ECR: 0.16 mol) and 9 mL of a water phase. The amount of water entrained in ECR was 0.5 time a mass of ECR.

Step (I-3): Added dropwise into the distillation residue solution obtained in the step (I-2) were the ECR distillate obtained in the step (I-2) and 103 g (0.62 mol; 18% on the basis of a whole amount of formaldehyde used) of a 18% by mass formaldehyde (F2) aqueous solution at 96° C. over 48 minutes and 90 minutes, respectively. After completion of the dropping, the resulting mixture was further heated at 100° C. for 60 minutes to allow a production reaction of di-TMP to proceed.

As a result of analyzing the resulting reaction solution (A1) by GC, it was confirmed that TMP, di-TMP and bis-TMP were produced in amounts of 90.5 g, 18.8 g and 2.8 g, respectively, and the yields of TMP, di-TMP and bis-TMP were 67.5%, 15.0% and 2.0%, respectively, on the basis of NBD as the raw material.

Next, the reaction solution (A1) was distilled to remove unreacted formaldehyde therefrom and then extracted with NBD. As the distillation apparatus used in step (II) for removing the unreacted formaldehyde, there was used a plate type distillation column in which a bottom pressure and a bottom temperature were adjusted to 0.3 MPa and 140° C., respectively. The extraction in the step (III) was carried out using NBD as an extractant in an amount equal to the amount of the reaction solution obtained after removing the unreacted formaldehyde. The water phase thus separated was further extracted with NBD, and the extraction was repeated 5 times. All of the five organic phases thus recovered by the extraction were mixed.

Then, after removing NBD used as the extractant (Y1) by distillation, the reaction solution was distilled to separate purified TMP therefrom and obtain a di-TMP-containing solution (B1). The distillation apparatus used in step (IV) for removing NBD was a plate type distillation column in which a bottom pressure and a bottom temperature were adjusted to 68 kPa and 135° C., respectively. Also, the distillation apparatus used in step (V) for separating the purified TMP was a film evaporator in which a bottom pressure and a bottom temperature were adjusted to 1.2 kPa and 170° C., respectively.

The obtained di-TMP-containing solution (B1) had the following composition.

| TMP | 3.5% by mass |
| di-TMP | 60.0% by mass |
| bis-TMP | 12.0% by mass |
| tri-TMP | 8.0% by mass |
| Other organic by-products | 16.5% by mass |
| Inorganic salts | 0.1% by mass |

The di-TMP-containing solution (B1) contained bis-TMP and tri-TMP in amounts of 20 parts by mass and 13.3 parts by mass, respectively, on the basis of 100 parts by mass of di-TMP.

Example 1

<Production of Di-TMP-Containing Solution (B2)>

Using a distillation facility equipped with a rectifying column (filler: "BX" available from Sulzer Chemtech Ltd.) having a theoretical plate number of 5 and a vertical thin-film distiller ("WIPRENE" available from Kobelco Solutions Co., Ltd.) as an evaporator, the di-TMP-containing solution (B1) obtained in Production Example 1 was distilled. The operating conditions were a bottom pressure of 0.4 kPa, a bottom temperature of 280° C. and a reflux ratio of 1. The di-TMP-containing solution (B2) obtained as a distillate had the following composition.

| TMP | 9% by mass |
| di-TMP | 80% by mass |
| bis-TMP | 2% by mass |
| tri-TMP | 0.04% by mass |
| Other organic by-products | 9% by mass |
| Inorganic salts | Not detected |

The di-TMP-containing solution (B2) contained bis-TMP and tri-TMP in amounts of 2.5 parts by mass and 0.05 parts by mass, respectively, on the basis of 100 parts by mass of di-TMP.

<Crystallization Under Pressure from Di-TMP-Containing Solution (B2)>

A 500 mL autoclave equipped with a reflux condenser, a thermometer and an electromagnetic stirrer was charged with 50 g of the thus obtained di-TMP-containing solution (B2) and 150 g of acetone having a boiling point of 56° C. as measured under normal pressures, followed by fully replacing an inside atmosphere of the autoclave with nitrogen. Then, the contents of the autoclave were heated to 85° C. using a mantle heater under an initial pressure of 0.2 MPa while stirring, and thereafter held at that temperature for 30 minutes. While continuously stirring, the mantle heater was detached from the autoclave, and the contents of the autoclave were cooled at a rate of 1.0° C./min until reaching a temperature of 30° C. Thereafter, while still maintaining the temperature of 30° C., the contents of the autoclave were subjected to crystallization over 1.5 hours, and then the stirring was stopped and the autoclave was opened to recover a slurry. The resulting slurry was subjected to filtration under reduced pressure using a glass filter (G-4) to separate the acetone solvent therefrom. The crystals recovered on the glass filter were washed with 50 g of acetone to obtain white crystals. The time required for the filtration was 2 minutes, and the obtained crystals were free from occurrence of cracks or the like.

The crystals were recovered in a petri dish and dried at 70° C., thereby obtaining 34.5 g of dried crystals. The resulting crystals contained di-TMP at a purity of 98.7%, and had a thick plate shape. The recovery rate of di-TMP from the di-TMP contained in the di-TMP-containing solution (B2) was 85%, and the phthalic acid resin color was 1.0.

Example 2

<Crystallization Under Pressure from Di-TMP-Containing Solution (B2)>

A 500 mL autoclave equipped with a stirrer, a thermometer and a reflux condenser was charged with 50 g of the di-TMP-containing solution (B2) obtained in Example 1 and 150 g of acetone, and an inside of the autoclave was pressurized by introducing nitrogen at 25° C. thereinto such that an initial pressure in the autoclave was 0.18 MPa. Then, the contents of the autoclave were heated to 85° C. while stirring, and thereafter held at that temperature for 30 minutes. While continuously stirring, the reaction pressure within the autoclave was gradually reduced, and the solvent evaporated was cooled by a cooler and recovered. The thus recovered solvent was fed back to the autoclave to cool the contents of the autoclave. The reaction pressure was controlled such that the cooling rate was 1.0° C./min.

After reaching normal pressures, the pressure within the autoclave was reduced using a vacuum pump to further cool the contents of the autoclave. The cooling rate under reduced pressure was also controlled to 1.0° C./min, and the pressure within the autoclave was allowed to finally reach 27 kPa. The temperature of the reaction solution subjected to the crystallization was 30° C. when the pressure reached 27 kPa. While maintaining the pressure within the autoclave at 27 kPa, the crystallization was continued for 1.5 hours, and then the pressure within the autoclave was increased until reaching normal pressures.

The resulting slurry was subjected to filtration under reduced pressure using a glass filter (G-4) to separate the solvent therefrom. The crystals recovered on the glass filter were washed with 50 g of acetone to obtain white crystals. The obtained crystals were free from occurrence of cracks or the like. The crystals were recovered in a petri dish and dried at 70° C., thereby obtaining 34.5 g of dried crystals. The resulting crystals contained di-TMP at a purity of 98.7%. The recovery rate of di-TMP from the di-TMP contained in the di-TMP-containing solution (B2) was 85%, and the phthalic acid resin color was 1.0.

Example 3

<Crystallization Under Pressure from Di-TMP-Containing Solution (B2)>

A 200 L SUS crystallization vessel equipped with a reflux condenser and a thermometer was charged with 30 kg of the di-TMP-containing solution (B2) obtained in Example 1 and 90 kg of acetone, and the contents of the crystallization vessel were heated to 85° C. At this time, an inside of the reaction system was pressurized to 0.18 MPa and held at that pressure for 30 minutes. The contents of the crystallization vessel were completely dissolved to form a uniform solution. The cooling rate was 1.0° C./min. The cooling was carried out by the method in which the solvent evaporated was cooled and fed back to the crystallization vessel until reaching 45° C./50 kPa, and by the method in which cold water was allowed to pass through a jacket in the temperature range of from 45 to 25° C. The contents of the crystallization vessel were held at 25° C. for 1 hour, and then subjected to filtration under reduced pressure. The resulting filter cake was washed with the same amount of acetone and dried at 70° C. The recovery rate of di-TMP from the di-TMP contained in the di-TMP-containing solution (B2) was 86.0%. The purity of di-TMP thus obtained was 98.5%, and the phthalic acid resin color was 1.0.

Comparative Example 1

<Crystallization Under Pressure from Di-TMP-Containing Solution (B1)>

The same procedure as in <Crystallization under Pressure from di-TMP-Containing Solution (B2)> of Example 1 was repeated except for using the di-TMP-containing solution (B1) obtained in Production Example 1 as the raw material. However, no precipitation of crystals was recognized.

Comparative Example 2

<Crystallization Under Normal Pressures from Di-TMP-Containing Solution (B1)>

A 500 mL round bottom flask equipped with a reflux condenser, a thermometer and a mechanical stirrer was charged with 100 g of the di-TMP-containing solution (B1) obtained in Production Example 1 and 150 g of acetone, and the contents of the flask were heated to 60° C. while stirring, thereby obtaining a brown solution. The resulting brown solution was cooled at a rate of 2.0° C./min while stirring until reaching a temperature of 30° C. and then subjected to crystallization over 1.5 hours while still maintaining the solution at 30° C., and thereafter the stirring was stopped to recover a slurry. The resulting slurry was in a creamy state and subjected to filtration under reduced pressure using a glass filter (G-4) to separate the solvent therefrom, thereby obtaining crystals. The obtained crystals suffered from cracking in the course of the filtration, so that it was not possible to continue the filtration procedure. The crystals recovered were re-slurried by adding 100 g of acetone thereto, and then the resulting slurry was subjected again to filtration under reduced pressure, and then the obtained filter cake was washed two times. The resulting crystals suffered from cracking and solidification similarly to those obtained in the preceding filtration. Further, the crystals were formed into blocks after dried and therefore difficult to handle.

Comparative Example 3

<Crystallization Under Pressure from Di-TMP-Containing Solution (B1)>

A 500 mL autoclave equipped with a reflux condenser, a thermometer and a stirrer was charged with 100 g of the di-TMP-containing solution (B1) obtained in Production Example 1 and 150 g of acetone, followed by fully replacing an inside atmosphere of the autoclave with nitrogen. Then, the contents of the autoclave were heated to 85° C. using a mantle heater under an initial pressure of 0.2 MPa while stirring, and thereafter held at that temperature for 30 minutes. While continuously stirring, the mantle heater was detached from the autoclave, and the contents of the autoclave were cooled at a rate of 1.0° C./min until reaching a temperature of 30° C. Thereafter, while still maintaining the temperature of 30° C., the contents of the autoclave were subjected to crystallization over 1.5 hours, and then the stirring was stopped and the autoclave was opened to recover a slurry. The resulting slurry was in a creamy state and subjected to filtration under reduced pressure using a glass filter (G-4) to separate the solvent therefrom. However, the crystals on the filter suffered from cracking. The crystals recovered on the glass filter were re-slurried and washed with 100 g of acetone two times to obtain white crystals. Both the solid-liquid separation and the re-slurrying required a prolonged time. The crystals were recovered in a petri dish and dried at 70° C., thereby obtaining 38 g of block-shaped crystals. The purity of di-TMP in the crystals was 87.5%, and the phthaiic acid resin color was 3.0. The recovery rate of di-TMP from the di-TMP contained in the di-TMP-containing solution (B1) was 41.5%.

Comparative Example 4

<Crystallization Under Normal Pressures from Di-TMP-Containing Solution (B2)>

A 500 mL round bottom flask equipped with a reflux condenser, a thermometer and a mechanical stirrer was charged with 50 g of the di-TMP-containing solution (B2) obtained in Example 1 and 150 g of acetone (solvent ratio: 3.0), and the contents of the flask were heated to 60° C. while stirring. However, it was not possible to completely dissolve the crystals.

Comparative Example 5

<Crystallization Under Normal Pressures from Di-TMP-Containing Solution (B2)>

A 500 mL round bottom flask equipped with a reflux condenser, a thermometer and a mechanical stirrer was charged with 50 g of the di-TMP-containing solution (B2) obtained in Example 1 and 250 g of acetone (solvent ratio: 5.0), and the contents of the flask were heated to 60° C. while stirring. However, it was not possible to completely dissolve the crystals.

Comparative Example 6

<Crystallization Under Normal Pressures from Di-TMP-Containing Solution (B2)>

A 500 mL round bottom flask equipped with a reflux condenser, a thermometer and a mechanical stirrer was charged with 25 g of the di-TMP-containing solution (B2) obtained in Example 1 and 250 g of acetone, and the contents of the flask were heated to 60° C. while stirring, thereby obtaining a light yellow solution. The resulting light yellow solution was cooled at a rate of 1.0° C./min while stirring until reaching a temperature of 30° C. and then subjected to crystallization over 1.5 hours while still maintaining the solution at 30° C., and thereafter the stirring was stopped to obtain a slurry. The resulting slurry was subjected to filtration and washing in the same manner as in Example 1, thereby obtaining crystals. The obtained crystals were free from cracking and kept in a good state. The crystals were then dried to recover 15 g of white crystals. The recovery rate of di-TMP from the di-TMP contained in the di-TMP-containing solution (B2) was 73.5%. The purity of di-TMP in the crystals was 98.1%, and the phthalic acid resin color was 1.0.

Comparative Example 7

<Rapid Cooling Crystallization After Crystallization Under Pressure from Di-TMP-Containing Solution (B2)>

The same procedure as in <Crystallization under Pressure from di-TMP-Containing Solution (B2)> of Example 1 was repeated except that the crystallization was rapidly carried out at a cooling rate of 3.0° C./min. The obtained crystals were acicular fine crystals, and the time required for solid-liquid separation thereof was 5 times that required in Example 1. The recovery rate of di-TMP from the di-TMP contained in the di-TMP-containing solution (B2) was 82.3%. The purity of di-TMP in the crystals was 96.1%, and the phthalic acid resin color was 2.0.

The operating conditions of the crystallization step (step (VII)) in the respective Examples and Comparative Examples as well as various properties of the di-TMP crystals obtained therein are shown in Table 1. In Table 1, the expression "not dissolved" appearing with respect to Comparative Examples 4 and 5 means that the conditions upon initiation of the crystallization failed to prepare a uniform solution, so that the crystallization step was unable to be performed. In Comparative Example 6, since the solvent ratio was increased, it was possible to dissolve the crystals and perform the crystallization, but the recovery rate of the crystals was lowered. In Comparative Example 7 in which the cooling rate was increased, the resulting crystals were acicular crystals, and it was therefore difficult to subject the crystals to filtration. In Comparative Examples 1 to 3 in which the distillation still residue obtained upon production of the purified TMP was not distilled but was directly subjected to the crystallization step, even if the crystallization step was able to be performed, the resulting slurry was in a creamy state, and it was therefore difficult to subject the slurry to filtration, and further the resulting crystals had a low purity.

TABLE 1

|  | Examples ||| Comparative Examples |||||||
|---|---|---|---|---|---|---|---|---|---|---|
|  | 1 | 2 | 3 | 1 | 2 | 3 | 4 | 5 | 6 | 7 |
| Operating conditions of step (VII) (crystallization step) | | | | | | | | | | |
| (1) Amount of solution fed | | | | | | | | | | |
| Distillation still residue of purified TMP (B1: g) | | | | 50 | 100 | 100 | | | | |
| Distillate of B1 (B2: g) | 50 | 50 | 30000 | | | | 50 | 50 | 25 | 50 |
| (2) Amount of solvent for crystallization (acetone) (g) | 150 | 150 | 90000 | 150 | 150 | 150 | 150 | 250 | 250 | 150 |
| (3) Crystallization initiation pressure (MPa) | 0.2 | 0.18 | 0.18 | 0.2 | *1) | 0.2 | *1) | *1) | *1) | 0.2 |
| (4) Crystallization initiation temperature (° C.) | 85 | 85 | 85 | 85 | 60 | 85 | 60 | 60 | 60 | 85 |
| (5) Retention time of crystallization initiation temperature (min) | 30 | 30 | 30 | 30 | 30 | 30 | | | 30 | 30 |
| (6) Cooling rate (° C./min) | 1.0 | 1.0 | 1.0 | 1.0 | 2.0 | 1.0 | | | 1.0 | 3.0 |
| (7) Crystallization termination temperature (° C.) | 30 | 30 | 25 | 30 | 30 | 30 | | | 30 | 30 |
| (8) Retention time of crystallization termination temperature (h) | 1.5 | 1.5 | 1.0 | 1.5 | 1.5 | 1.5 | | | 1.5 | 1.5 |
| Condition of slurry, etc. | *2) | *2) | *2) | *3) | *4) | *4) | *5) | *5) | *2) | *6) |
| Evaluation results of di-TMP crystals | | | | | | | | | | |
| (1) Recovery rate (%) | 85.0 | 85.0 | 86.0 | | 35.0 | 41.5 | | | 73.5 | 82.3 |
| (2) Purity (%) | 98.7 | 98.7 | 98.5 | | 84.7 | 87.5 | | | 98.1 | 96.1 |

TABLE 1-continued

|  | Examples | | | Comparative Examples | | | | | | |
| --- | --- | --- | --- | --- | --- | --- | --- | --- | --- | --- |
|  | 1 | 2 | 3 | 1 | 2 | 3 | 4 | 5 | 6 | 7 |
| (3) Phthalic acid resin color | 1.0 | 1.0 | 1.0 |  | 4.0 | 3.0 |  |  | 1.0 | 2.0 |
| (4) Condition of crystals | *7) | *7) | *7) |  | *8) | *8) |  |  | *7) | *9) |

Note
*1) Under normal pressures;
*2) Normal;
*3) Not crystallized;
*4) Creamy;
*5) Not dissolved;
*6) Filtration time was 5 times that in Example 1;
*7) Plate-shaped;
*8) Block-shaped;
*9) Fine acicular shape As is apparent from the above Examples, in the present invention, when distilling crude TMP to separate TMP as a distillate and obtain a distillation still residue containing a large amount of di-TMP, further distilling the distillation still residue to obtain a di-TMP-containing solution containing less amounts of bis-TMP and tri-TMP and then subjecting the di-TMP-containing solution to crystallization with an organic solvent, (1) the specific raw materials for the crystallization are used, and (2) the crystallization is initiated under pressure at a temperature exceeding a boiling point of the organic solvent and the crystallization system is cooled at a rate of 2° C./min or less. As a result, it is possible to readily obtain a colorless high-purity di-TMP with a high recovery rate.

Industrial Applicability

In accordance with the present invention, it is possible to produce a high-purity di-TMP from crude di-TMP produced upon production of TMP with a high recovery rate in a simple, industrially useful manner, and the resulting di-TMP can be effectively used as a raw material for polyacrylates, polyether polyols, polyurethanes, alkyd resins, synthetic lubricants or the like.

The invention claimed is:

1. A method for producing ditrimethylolpropane (di-TMP) by recovering the di-TMP from a reaction solution containing trimethylolpropane (TMP), the di-TMP, tritrimethylolpropane (tri-TMP) and bistrimethylolpropane (bis-TMP), which is produced by reacting n-butyl aldehyde and formaldehyde in the presence of a base catalyst, said method comprising:
   (I) reacting n-butyl aldehyde and formaldehyde in the presence of the base catalyst to obtain the reaction solution (A1) containing the TMP, the di-TMP, and the bis-TMP and/or the tri-TMP as by-products;
   (II) distilling the reaction solution (A1) to remove unreacted formaldehyde therefrom and obtain the TMP-containing solution (A2);
   (III) subjecting the TMP-containing solution (A2) to extraction with the organic solvent (Y1) to separate a reaction product-containing extract therefrom;
   (IV) distilling the extract obtained in (III) to remove the organic solvent (Y1) therefrom and obtain the crude TMP (A3);
   (V) distilling the crude TMP (A3) to separate the purified TMP (A4) therefrom and obtain a di-TMP-containing solution (B1) from the distillation still residue;
   (VI) further distilling the di-TMP-containing solution (B1) to separate a di-TMP-containing solution (B2) as a distillate therefrom; and
   (VII) subjecting the di-TMP-containing solution (B2) to crystallization with the organic solvent (Y2) containing an aliphatic ketone to obtain di-TMP (B3);

said method being carried out under the following conditions (1) and (2):
   (1) the di-TMP-containing solution (B2) obtained in (VI) contains the bis-TMP and the tri-TMP in amounts of 10 parts by mass or less and 5 parts by mass or less, respectively, on the basis of 100 parts by mass of the di-TMP; and
   (2) in (VII), the crystallization is initiated under pressure at a temperature exceeding a boiling point of the organic solvent (Y2) as measured under normal pressures, and the resulting crystallization product solution is cooled at a temperature drop rate of 2° C./min or less.

2. The method for producing ditrimethylolpropane according to claim 1, wherein (VI) is carried out using a distiller constructed from combination of a thin-film evaporator and a rectifying column, and a bottom pressure of the distiller upon further distilling the di-TMP-containing solution (B1) in (VI) is from 0.1 to 1.0 kPa.

3. The method for producing ditrimethylolpropane according to claim 1, wherein a bottom temperature of the distiller upon further distilling the di-TMP-containing solution (B1) in (VI) is from 250 to 300° C.

4. The method for producing ditrimethylolpropane according to claim 1, wherein the organic solvent (Y2) used in (VII) is acetone.

5. The method for producing ditrimethylolpropane according to claim 1, wherein in (VII), a mass ratio of the organic solvent (Y2) to the di-TMP-containing solution (B2) [organic solvent (Y2)/di-TMP-containing solution (B2)] is from 0.5 to 20.

6. The method for producing ditrimethylolpropane according to claim 1, wherein a temperature upon initiation of the crystallization in (VII) is from 70 to 90 ° C.

7. The method for producing ditrimethylolpropane according to claim 1, wherein a pressure upon initiation of the crystallization in (VII) is from 0.11 to 0.3 MPa.

8. The method for producing ditrimethylolpropane according to claim 1, wherein in (VII), the crystallization initiation temperature is held for a time period of from 0.1 to 5 hours.

9. The method for producing ditrimethylolpropane according to claim 1, wherein a temperature upon termination of the crystallization in (VII) is from 40 to 20 ° C.

10. The method for producing ditrimethylolpropane according to claim 1, wherein a pressure upon termination of the crystallization in (VII) is from 100 to 20 kPa.

11. The method for producing ditrimethylolpropane according to claim 1, wherein the organic solvent (Y2) vaporized in (VII) is cooled and fed back to the crystallization system to remove heat generated upon the crystallization.

* * * * *